United States Patent
Gidwani et al.

(10) Patent No.: US 6,828,334 B2
(45) Date of Patent: Dec. 7, 2004

(54) FENOFIBRATE-CYCLODEXTRIN INCLUSION COMPLEXES AND THEIR PHARMACEUTICAL COMPOSITION

(75) Inventors: Suresh Kumar Gidwani, Mumbai (IN); Purushottam Sharshikant Singnurkar, Jalgaon (IN)

(73) Assignee: USV Limited, Mumbai (IN)

( * ) Notice: Subject to any disclaimer, the term of this patent is extended or adjusted under 35 U.S.C. 154(b) by 0 days.

(21) Appl. No.: 10/338,562

(22) Filed: Jan. 7, 2003

(65) Prior Publication Data

US 2003/0220293 A1 Nov. 27, 2003

Related U.S. Application Data

(60) Provisional application No. 60/382,997, filed on May 23, 2002.

(51) Int. Cl.$^7$ .............................. A61K 9/00; A61K 9/14
(52) U.S. Cl. ..................... 514/338; 514/326; 514/369; 514/58; 514/60; 514/557; 514/772.2; 514/772.3; 514/773; 514/777; 514/779; 514/781; 424/451; 424/489; 424/462; 424/464; 424/440; 424/493; 424/500; 536/103; 536/120; 536/122

(58) Field of Search ................... 514/338, 326, 514/369, 58, 60, 557, 772.2, 772.3, 773, 777, 779, 781; 424/451, 489, 462, 464, 440, 493, 500, 96; 536/103, 120, 122

(56) References Cited

U.S. PATENT DOCUMENTS 6,277,405 B1 * 8/2001 Stamm et al. ............... 424/462
6,464,988 B1 * 10/2002 Gidwani et al. ............ 424/400

* cited by examiner

*Primary Examiner*—James O. Wilson
*Assistant Examiner*—Devesh Khare
(74) *Attorney, Agent, or Firm*—Gibbons, Del Deo, Dolan, Griffinger & Vecchione

(57) ABSTRACT

The present invention relates to pharmaceutical compositions containing fenofibrate in the form of an inclusion complex with cyclodextrin, having high dissolution profile and in vivo enhanced bioavailability as compared with plain micronized fenofibrate compositions. An inclusion complex has a molar ratio of fenofibrate (preferably in micronized form) to cyclodextrin of from about 1:0.5 to about 1:4, preferably from about 1:1 to about 1:2. The immediate release fenofibrate composition is preferably in the form of a tablet or in the form of granules inside a capsule.

20 Claims, 2 Drawing Sheets

FENOFIBRATE-CYCLODEXTRIN INCLUSION COMPLEXES AND THEIR PHARMACEUTICAL COMPOSITION

CROSS-REFERENCE TO COPENDING PATENT APPLICATIONS

The present application claims the benefit of U.S. provisional application No. 60/382,997, filed on May 23, 2002 which is incorporated herein by reference in its entirety.

FIELD OF THE INVENTION

The present invention relates to novel pharmaceutical compositions having a high dissolution profile. In particular, the invention relates to compositions including cyclodextrin, inclusion complexes and methods for preparing the same.

BACKGROUND OF THE INVENTION

Fenofibrate corresponds to the nomenclature of 2-[4-(4-chlorobenzoyl)phenoxy]-2-methyl propionate and is insoluble in water. Fenofibrate has the formula:

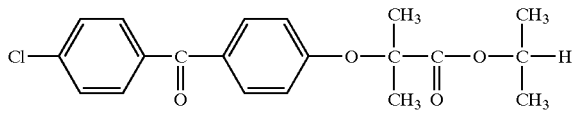

With an aqueous solubility of less than 0.5 mg/liter, the dissolution of fenofibrate likely represents the rate limiting steps before the drug becomes adsorbed in the body. Fenofibrate is a neutral, lipophilic compound having a lipid water distribution coefficient, log P=5.24, and is a well-known hypolipemiant from the family of fibrates, which is commercially available in various doses (100 and 300 mg for example Secalip®) but in a form leading to poor bioavailability of the active ingredient.

Bioavailability is the degree to which or rate at which a drug or other substance is absorbed or becomes available at the site of physiological activity after administration. Drugs having a high dissolution profile have a higher bioavailability than drugs that have a low dissolution profile. A hypolipemiant is a drug that reduces the amount of lipids (fats) in the blood. Lipophilic is a substance having affinity for, tending to combine with, or capable of dissolving in lipids. Fenofibrate is both hypolipemiant and lipophilic. Due to its poor hydrosolubility (solubility in water), however, fenofibrate is poorly absorbed in the digestive tract and consequently its bioavailability is incomplete, irregular and often varies from one person to another. As a result, commercially available doses must be of higher strength and require application several times a day.

EPA-0330532 to Curtet et al., describes a method for improving bioavailability of fenofibrate by co-micronizing fenofibrate with a surfactant, for example sodium lauryl sulphate, in order to improve fenofibrate solubility. According to this invention, 200 mg of co-micronized fenofibrate was found to be bioequivalent to 300 mg of non-micronized fenofibrate. However, this improvement in dissolution and bioavailability is not satisfactory because the technique of co-micronizing with a surfactant still leads to incomplete dissolution of fenofibrate.

U.S. Pat. No. 6,277,405 B 1 to Stamm, et al., describes a fenofibrate pharmaceutical composition having enhanced bioavailability . It comprises spraying a suspension of a micronized fenofibrate with hydrophilic polymer, for example, polyvinyl pyrrolidone onto an inert carrier. Following granulation, the granulate formed consists of crystals of, for example, lactose which are isolated and particles of micronized fenofibrate and PVP adhere to the crystal surface. The granulate obtained is compressed to form tablets. This composition has been shown to have a dissolution of at least 10% in 5 minutes, 20% in 10 minutes, 50% in 20 minutes and 75% in 30 minutes as measured by using the rotating blade method at 75 rpm, in a dissolution medium constituted by water with 2% by weight polysorbate 80 or with 0.025 M sodium lauryl sulphate. Although the composition described in the '405 patent appears to show improved bioavailability, its method of preparation is complex and expensive. For example, the process described by Stamm et al. involves spray coating of fenofibrate with polyvinyl pyrrolidone onto an inert carrier. This process not only involves the material loss of fenofibrate but also requires expensive equipment such as a fluidized bed coater/granulator that is difficult to scale up for a commercial product.

U.S. Pat. No. 6,294,192 To Patel, et al, describes triglyceride free compositions and methods for improved delivery of hydrophobic therapeutic agent, for example fenofibrate. Prepared by simple physical mixing, the compositions include a hydrophobic therapeutic agent and a carrier, where the carrier is formed from a combination of a hydrophilic surfactant and a hydrophobic surfactant. Upon dilution with an aqueous solvent, the composition forms a clear aqueous dispersion of the surfactant containing a hydrophobic therapeutic agent. Patel et al. also refer to fenofibrate as one of the hydrophobic therapeutic agent but do not provide any bioavailability improvement data on fenofibrate. The carrier described in Patel et al. further comprises cyclodextrin or cyclodextrin derivatives as an additional solubilizer to enhance the solubility of the hydrophobic therapeutic agent and not as the carrier itself. Further, Patel et al. do not provide any information or data for the use and effect of such solubilizers and their concentrations. By gently mixing or shaking the cyclodextrin with the carrier, the drug employed in the compositions of Patel et al. gains only marginal improvement in solubility (dissolution) and/or bioavailability.

This invention provides an inclusion complex of fenofibrate with cyclodextrin, the complex having enhanced bioavailability as compared to either fenofibrate alone or a suspension of a micronized fenofibrate with hydrophilic polymer, such a s PVP. As such, the present invention overcomes the limitations still existing in available fenofibrate products so as to improve the dissolution profile, improve absorption characteristics improve bioavailability of fenofibrate and reduce the dose required for administration to attain a desired effect as compared to that for a fenofibrate pharmaceutical composition that is not part of a complex with cyclodextrin. Thus, there is still a need to provide fenofibrate pharmaceutical compositions and dosage forms having enhanced bioavailability where the dissolution of fenofibrate in the body is increased to a level of 100% within a short period of time after administration in comparison to a level of dissolution that fenofibrate has by itself, before it forms an inclusion complex with cyclodextrin. That is, the fenofibrate pharmaceutical composition has a characteristic that allows a dosage form of the inclusion complex of fenofibrate with cyclodextrin to be completely dissolved within a short time after administration.

SUMMARY OF THE INVENTION

An aspect of the present invention resides in providing an immediate release pharmaceutical composition comprising an inclusion complex of fenofibrate with cyclodextrin which complex shows rapid and complete dissolution of fenofibrate, resulting into enhanced bioavailability.

Another aspect of the invention resides in a method for the preparation of an inclusion complex of fenofibrate with cyclodextrin which is efficient and economical, simple and less time consuming than conventional techniques, and which is suitable for manufacture of a product on commercial scale.

Preferably, the complex of fenofibrate with cyclodextrin renders the active drug fenofibrate highly soluble and/or rapidly dissoluble in physiological fluids including gastric fluid. Dissolution levels of fenofibrate can reach from about 80% to about 100% in a relatively short amount of time from about 10 to about 30 minutes, preferably from about 10 to about 20 minutes.

A further aspect of the present invention is to provide pharmaceutical compositions of an inclusion complex of fenofibrate with cyclodextrin, which renders the active drug fenofibrate highly soluble and/or rapidly dissoluable and safe for use as a pharmaceutical.

Still another aspect of the present invention is to provide a method for the preparation of pharmaceutical compositions having an inclusion complex of fenofibrate with cyclodextrin, which results in a product safe for use as a pharmaceutical and which renders the active drug fenofibrate highly soluble in physiological as well as in gastric fluid pH.

Other improvements which the present invention provides over the prior art will be identified as a result of the following description which sets forth the preferred embodiments of the present invention. The description is not in any way intended to limit the scope of the present invention, but rather only to provide a working example of the presently preferred embodiments. The scope of the present invention will be pointed out in the appended claims.

DETAILED DESCRIPTION OF THE INVENTION

Figure 1A:
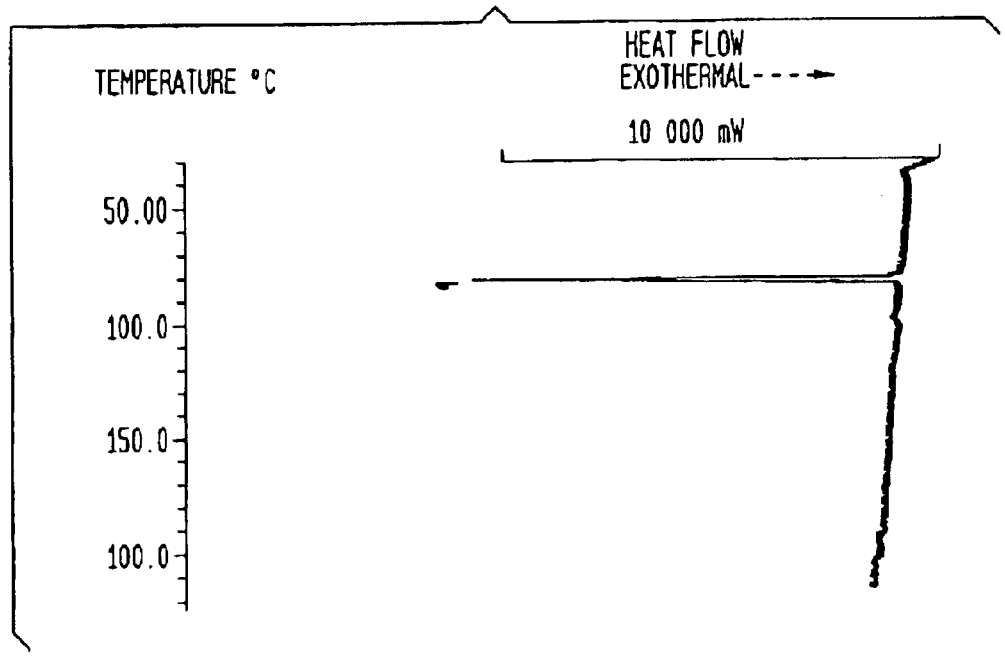
FIG. 1A is a DSC thermogram of fenofibrate.

According to the present invention there is provided a inclusion complex of 2-[4-(4-chlorobenzoyl)phenoxy]-2-methyl propanoic acid, commonly known as fenofibrate of the formula 1 below

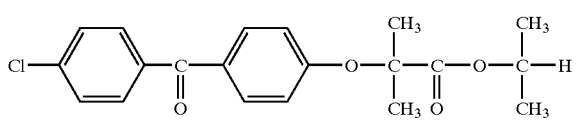

1 with cyclodextrin. In the inclusion complex of the invention, fenofibrate is in micronized form of average particle size from about 1 μm to about 40 μm, preferably from about 2 μm to about 20 μm and cyclodextrin has an average particle size of from about 10 μm to about 350 μm, preferably from 10 μm to about 250 μm. In the inclusion complex of the present invention the molar ratio of fenofibrate to cyclodextrin is from about 1:0.5 to about 1:4.

According to the invention there is also provided a method for the preparation of a cyclodextrin inclusion complex of fenofibrate which comprises:

a) wetting cyclodextrin or cyclodextrin derivative of average particle size from about 10 μm to about 250 μm with a solvent such as water, acetone, C1–C4 aliphatic alcohol (other than ethanol and other than rectified spirit); or mixtures of the foregoing solvents;

b) mixing the resulting semisolid mixture with fenofibrate of micronized average particle size of from about 1 μm to about 40 μm; and c) drying the mixed inclusion complex at from about 40° C. to about 80° C., the molar ratio of fenofibrate to cyclodextrin or cyclodextrin derivative being from about 1:0.5 to about 1:4, and the molar ratio of solvent to cyclodextrin or cyclodextrin derivative being from about 1:1.5 to about 1:4.

According to the present invention there are also provided pharmaceutical compositions of a cyclodextrin inclusion complex of fenofibrate in combination with pharmaceutically acceptable excipients, wherein the fenofibrate is in micronized average particle sizes of from about 1.0 μm to about 40 μm and the cyclodextrin or cyclodextrin derivative is in average particle sizes of from about 10 μm to about 250 μm and the molar ratio of fenofibrate to cyclodextrin or cyclodextrin derivative is from about 1:0.5 to about 1:4.

According to the invention there is also provided a method for the preparation of a pharmaceutical composition of a cyclodextrin inclusion complex of fenofibrate in combination with pharmaceutically acceptable excipients, wherein the fenofibrate is in a micronized form having an average particle size of from about 1.0 μm to about 40 μm and cyclodextrin or cyclodextrin derivative has an average particle size of from about 10 μm to about 250 μm, and the molar ratio of fenofibrate to cyclodextrin or cyclodextrin derivative is from about 1:0.5 to about 1:4, which method comprises mixing the inclusion complex with the excipients, and if desired, converting the resulting mixture into a desired pharmaceutical dosage form.

Preferably the average particle sizes of fenofibrate can be from about 2 μm to about 20 μm.

Cyclodextrins useful in the inclusion complex of the present invention include without limitation alpha cyclodextrin, beta cyclodextrin, gamma cyclodextrin, alkyl, hydroxy alkyl derivatives or mixtures thereof. Preferably cyclodextrin may be beta cyclodextrin, gamma cyclodextrin, hydroxypropyl beta cyclodextrin randomly methylated beta cyclodextrin, or mixtures thereof. As used herein, "cyclodextrins" refers to α-1,4 linked cyclic oligosaccharides composed of glucopyranose units. The number of glucoses forming the ring is not limited at all and α, β- and γ-cyclodextrins having 6 to 8 glucoses are commercially available. The cyclodextrin may have a branch. The hydroxyl group(s) in cyclodextrin may be modified; cyclodextrins having such a modifying group are included in the "modified derivatives of cyclodextrin". Illustratively, the modification includes alkylation such as methylation, hydroxyalkylation such as hydroxypropylation, esterification such as acetylation or succinylation, glucosylation, carboxymethyl etherification, phosphoric esterification, sulfobutyl etherification, and carboxymethylation. These modified derivatives are described in Loftsson et al., J. Pharmaceu. Sci., 85:1017 (1996); Stella et al., Pharmaceutical Res., 14:556 (1997).

Preferably water or isopropyl alcohol can be used as a solvent, either alone or in combination with each other. Whenever combinations are used, the water and isopropyl alcohol can be in a ratio of from about 1:9 to about 9:1, preferably from about 1:7.5 to about 7.5:1.

The inclusion complex can be freeze dried or spray dried or dried by low temperature vacuum evaporation in a tray dryer or dried in fluidized bed dryer. Preferably the mixed inclusion complex may be dried in tray dryer. Preferably drying is carried out at temperatures from about 40° C. to about 60° C.

The molar ratio of fenofibrate to cyclodextrin or cyclodextrin derivative is preferably from about 1:1 to about 1:2.

The molar ratio of solvent to cyclodextrin or cyclodextrin derivative can preferably be about 1:2.4.

Useful excipients for the fenofibrate-cyclodextrin inclusion complex include without limitations lactose, microcrystalline cellulose, calcium carbonate, starch, colloidal silicone dioxide, sodium starch glycolate, talc, magnesium stearate, polyvinyl pyrrolidone, mixtures thereof, and/or other excipients known in the art.

The fenofibrate-cyclodextrin inclusion complex can be administered as pharmaceutical formulations in form of tablet or in the form of granules inside a capsule. Tablets and capsules can be prepared by mixing the dried and sized fenofibrate complex with pharmaceutically acceptable excepients, and compressing the resulting blend into tablets or filling it into capsules. Tablets and capsules are prepared in accordance with the invention by employing the same techniques that are well known in the art for forming tablets and capsules composed of other types of ingredients.

If desired, the compositions may be encapsulated in a hard or soft gelatin capsule, a starch capsule or an enteric coated capsule. The term "enteric coated capsule" as used herein means a capsule coated with a coating resistant to acid, especially gastric acid. The unit dose of fenofibrate contained in each tablet can be from about 100 mg to about 300 mg. The unit dose of fenofibrate in each capsule can also be from about 100 mg to about 300 mg, or the amount of the unit does may be higher or lower as determined by a physician for use in administration to a patient in view of the patient's age, weight, and response to such administration. If desired, the capsule or tablet may be coated to enhance its appearance.

In a preferred embodiment, tablets or capsules including the fenofibrate-cyclodextrin inclusion complex of the present invention can be prepared by a method which comprises:

(i) wetting cyclodextrin or cyclodextrin derivative of particle sizes from about 10 μm to almost 250 μm with a pharmaceutically acceptable solvent such as water, acetone, and/or C1–C4 aliphatic alcohol (other than ethanol and other than rectified sprit) at room temperature to form a semisolid mixture;
(ii) mixing the resulting semisolid mixture with fenofibrate of micronised particle sizes of from about 1 μm to about 40 μm to form a mixed fenofibrate-cyclodextrin inclusion complex;
(iii) drying the mixed fenofibrate-cyclodextrin inclusion complex at from about 40° C. to about 80° C. to form the fenofibrate-cyclodextrin inclusion complex, the molar ratio of fenofibrate to cyclodextrin or cyclodextrin derivative being 1:(0.5–4), and the molar ratio of solvent to cyclodextrin or cyclodextrin derivative being 1:(1.5–4);
(iv) mixing the dried and sized fenofibrate complex with pharmaceutically acceptable excipients, and compressing the resulting blend into tablets or filling it into capsules.

The fenofibrate-cyclodextrin inclusion complex of of the invention is unreported hitherto and is novel. According to the invention, the fenofibrate is in micronized form having an average particle size suitable for interaction with cyclodextrin. The micronized fenofibrate has increased surface area for better interaction with cyclodextrin or cyclodextrin derivatives. The solvent used is in considerably less quantity then previously known in the art. For example, a solvent to cyclodextrin molar ratio of from about 1:1.5 to about 1:4 is sufficient to wet the cyclodextrin and result in a semisolid reaction mixture. The semisolid mixture of cyclodextrin is amenable to shear mixing with fenofibrate because of which it has been possible to obtain an inclusion complex in which the fenofibrate is uniformly distributed and dispersed in cyclodextrin matrix. The shear mixed inclusion complexes prepared by the method of the invention show rapid and high aqueous solubility of fenofibrate. For example, the shear mixed inclusion complexes show a 95% dissolution at physiological pH of 6.8 within 15 minutes and 100% dissolution in within 30 minutes, 70% dissolution in neutral pH of water within 30 minutes and 45% dissolution in pH of 1.2 (gastric fluid) within 30 minutes. Shear mixing is provided by methods well known in the art, for example by using a high shear mixer as manufactured by Diosna Mixer, West Germany or its equivalent.

The following experimental examples are illustrative of the best mode of the invention but not limited to the scope thereof. All the materials used in the examples below are commercially readily available.

EXAMPLE 1

The purpose of this example was to prepare of an inclusion complex of fenofibrate and beta cyclodextrin.

Beta cyclodextrin (504 gm) having an average particle size from about 10 μm to about 70 μm was mixed with 216 ml of demineralized water. The water:beta cyclodextrin ratio was 1:2.33. The reaction mixture was mixed in a suitable high shear mixer available from Diosna Mixer, West Germany or its equivalent to obtain a semisolid mixture. To the semisolid beta cyclodextrin mixture, fenofibrate (160 gm) milled to an average particle size of from about 2 μm to about 40 μm was added and mixed in a high shear mixer for 1 hour. The fenofibrate:beta cyclodextrin molar ratio was 1:1. The resulting semisolid mass was dried at from about 40° C. to about 60° C. to obtain a solid inclusion complex of fenofibrate with beta cyclodextrin.

EXAMPLE 2

An inclusion complex of fenofibrate and beta cyclodextrin was prepared according to a procedure analogous to that of Example 1. A mixture of isopropyl alcohol (80 ml) with water (120 ml) was used instead of demineralized water. The mixture of isopropyl alcohol and water was mixed with 504 gm of beta cyclodextrin to obtain an inclusion complex having a molar ratio of fenofibrate:beta cyclodextrin of about 1:1. The molar ratio of isopropyl alcohol with water mixture to beta cyclodextrin was 1:2.52.

EXAMPLE 3

The procedure of Example 1 was followed using beta cyclodextrin (1008 gm) to obtain an inclusion complex which had a molar ratio of fenofibrate:beta cyclodextrin of 1:2 and a molar ratio of water to beta cyclodextrin of 1:2.33.

EXAMPLE 4

The procedure of Example 1 was followed using hydroxypropyl beta cyclodextrin (670 gm) as manufactured by Cerestar Inc., USA to obtain an inclusion complex having a molar ratio of fenofibrate:hydroxypropyl beta cyclodextrin of 1:1 and a molar ratio of water to hydroxypropyl beta cyclodextrin of 1:3.72.

EXAMPLE 5

The procedure of Example 1 was followed using gamma cyclodextrin (575 gm) (Cerestar Inc., USA) to obtain an inclusion complex wherein the molar ratio of fenofibrate-:gamma cyclodextrin was 1:2 and the molar ratio of water-:gamma cyclodextrin ratio was 1:2.21.

EXAMPLE 6

The procedure of Example 1 was followed using randomly methylated beta cyclodextrin (590 gm) (Cerestar Inc., USA) to obtain an inclusion complex having a molar ratio of fenofibrate:gamma cyclodextrin of 1:1, and a ratio of water-:gamma cyclodextrin of 1:2.10.

EXAMPLE 7

The procedure of Example 1 was followed using isopropyl alcohol (230 ml) (MERCK KgaA, Germany) instead of demineralized water to obtain an inclusion complex. The isopropyl alcohol:beta cyclodextrin ratio was 1:2.19. The fenofibrate:beta cyclodextrin molar ratio was 1:1.

EXAMPLE 8

The procedure of Example 9 was followed using isopropyl alcohol (460 ml) and beta cyclodextrin (1008 gm) to obtain an inclusion complex wherein the molar ratio of fenofibrate:beta cyclodextrin was 1:2, and the molar ratio of isopropyl alcohol:beta cyclodextrin was 1:2.19.

EXAMPLE 9

The procedure of Example 6 was followed using hydroxypropyl beta cyclodextrin (670 gm) (Cerestar Inc., USA) and isopropyl alcohol. The resulting inclusion complex had a molar ratio of fenofibrate:hydroxypropyl beta cyclodextrin of 1:1, and a molar ratio of isopropyl alcohol:hydroxypropyl beta cyclodextrin of 1:3.72.

EXAMPLE 10

A pharmaceutical composition in tablet form comprising 160 mg of fenofibrate was prepared by homogeneously mixing the inclusion complex of Example 1 with the excipients set forth in Table 1 below:

TABLE 1

| Ingredients | Manufacturer | Contents in Tablet |
|---|---|---|
| Inclusion complex of Example 1 | | 664 mg |
| Microcrystalline cellulose | FMC International | 32 mg |
| Sodium starch glycolate | Avebe, Holand | 12 mg |
| Talc | Aldrich Chemical Co | 8 mg |
| Crosspovidone | BASF, USA | 12 mg |
| Colloidal silicone dioxide | Degussa, Germany | 4 mg |
| Magnesium stearate | Aldrich Chemical Co | 10 mg |

The ingredients set forth in Table 1 above are easily commercially available. Subsequently, the resulting pharmaceutical composition was directly compressed into tablets by methods well known in the art. For example, the tablet can be obtained on an alternating compression medicine (e.g., Korsch EKO) or a rotary machine (e.g., Fette Perfecta 2).

EXAMPLE 11

The fenofibrate tablets obtained in Example 13 were film coated with a film coating having the composition set forth in Table 2 below:

TABLE 2

| Ingredients | Contents in Tablet |
|---|---|
| Hydroxypropyl methyl cellulose E-15 | 8 mg |
| Polyethylene glycol | 0.62 mg |
| Propylene glycol | 0.62 mg |
| Talc | 4.7 mg |
| Titanium dioxide | 3.3 mg |
| Isopropyl alcohol | 43 mg |
| Water | 130 mg |

The above ingredients are easily commercially available. To coat the fenofibrate tablets, film coating procedures well known in the art were used. Tablets were coated in an Accela Coater by spraying the coating solution of the above composition at a flow rate of about 40 to about 80 ml per minute and a pressure of from about 4 to about 6 Kg/square cm. During coating the tablet bed temperature was kept at from about 35° C. to about 45° C. with air blower under exhaust throughout the coating process.

EXAMPLE 12

A pharmaceutical composition in capsule form comprising 160 mg of fenofibrate was prepared by homogeneously mixing the inclusion complex of Example 1 with the additives set forth in Table 3 below, before being filled into hard gelatin capsule of size 0, according to methods well known in the art. All ingredients listed below are easily commercially available from services as listed in Table 1.

TABLE 3

| Ingredients | Contents in Tablet |
|---|---|
| Inclusion complex of Example 1 | 664 mg |
| Microcrystalline cellulose | 32 mg |
| Sodium starch glycolate | 12 mg |
| Talc | 8 mg |
| Crosspovidone | 12 mg |
| Colloidal silicone dioxide | 4 mg |
| Magnesium stearate | 10 mg |

EXAMPLE 13

160 gm of fenofibrate was mixed with 504 gm of beta cyclodextrin to provide a mixture containing 160 mg of fenofibrate per 664 mg of mixture wherein the molar ratio of fenofibrate:beta cyclodextrin was 1:1.

EXAMPLE 14

In this example, the inclusion complex of Example 1 was characterized by high pressure liquid chromatography (HPLC), and differential scanning calorimetry (DSC).

A. Quantitative Determination of Fenofibrate Form Inclusion Complex by HPLC

The potency of inclusion complex was calculated by HPLC with the following parameters as listed in Table 4 below.

TABLE 4

| | |
|---|---|
| Mobile phase | Buffer:Acetonitrile (300:700) Buffer - 300 ml of water acidified to pH 2.5 with orthophosphoric acid |

TABLE 4-continued

| | |
|---|---|
| Flow rate | 1 ml per min. |
| Temperature | Room temperature |
| Column (specify manufacturer) | Inertsil C18, ODS-3, 250 mm × 4.6 mm, 5 μm column (Manufacturer: Gl Sciences Inc., Japan) |
| Detection wavelength | 286 nm |

The retention of fenofibrate was found to be 12.5 minutes for 32 mg of the inclusion complex of Example 1 which contained 5.01 mg of fenofibrate. This assay level proved that fenofibrate was uniformly dispersed through out the inclusion complex.

B. Differential Scanning Calorimetry Study

Figure 1B:
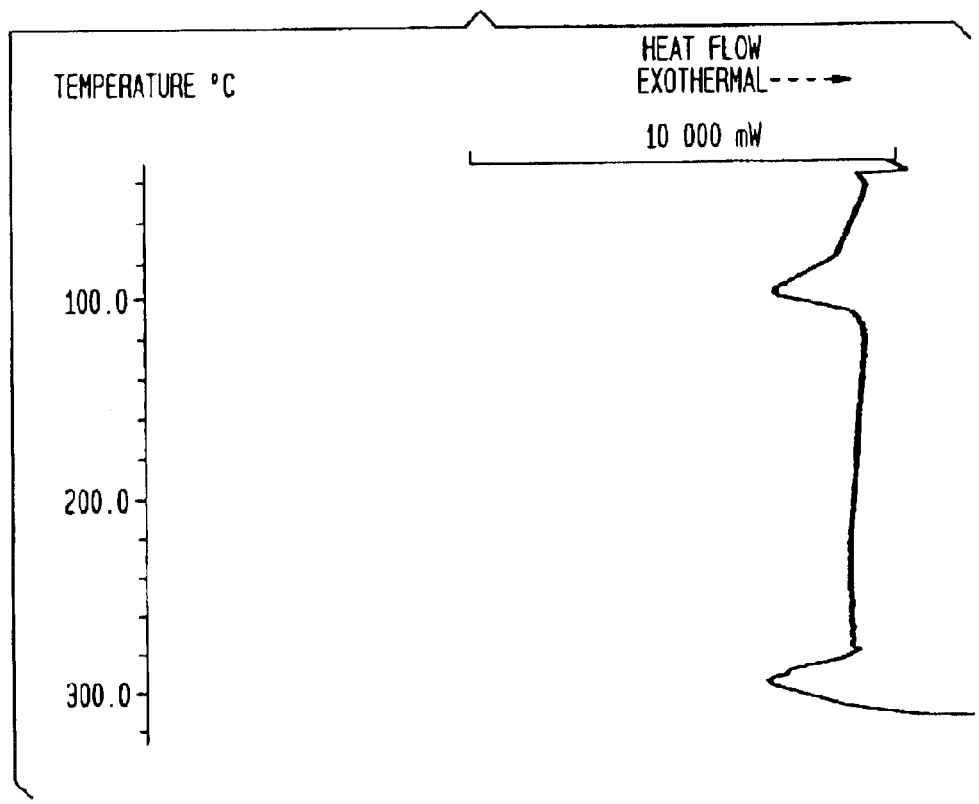
FIG. 1B is a DSC thermogram of beta cyclodextrin.
Figure 1C:
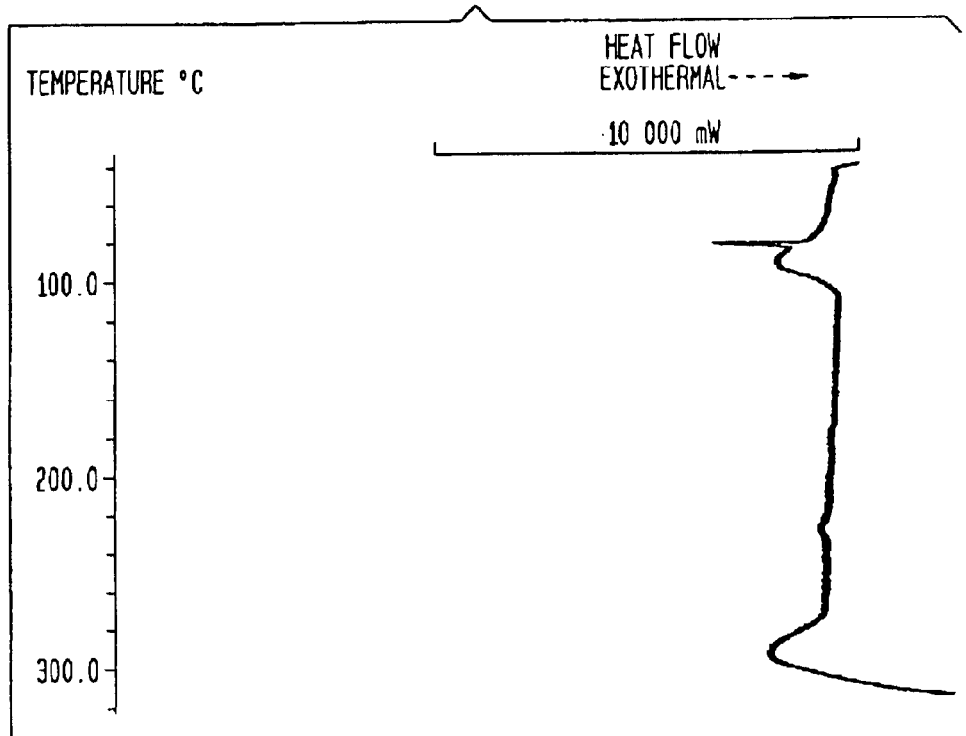
FIG. 1C is a DSC thermogram of a physical mixture of fenofibrate with beta cyclodextrin.
Figure 1D:
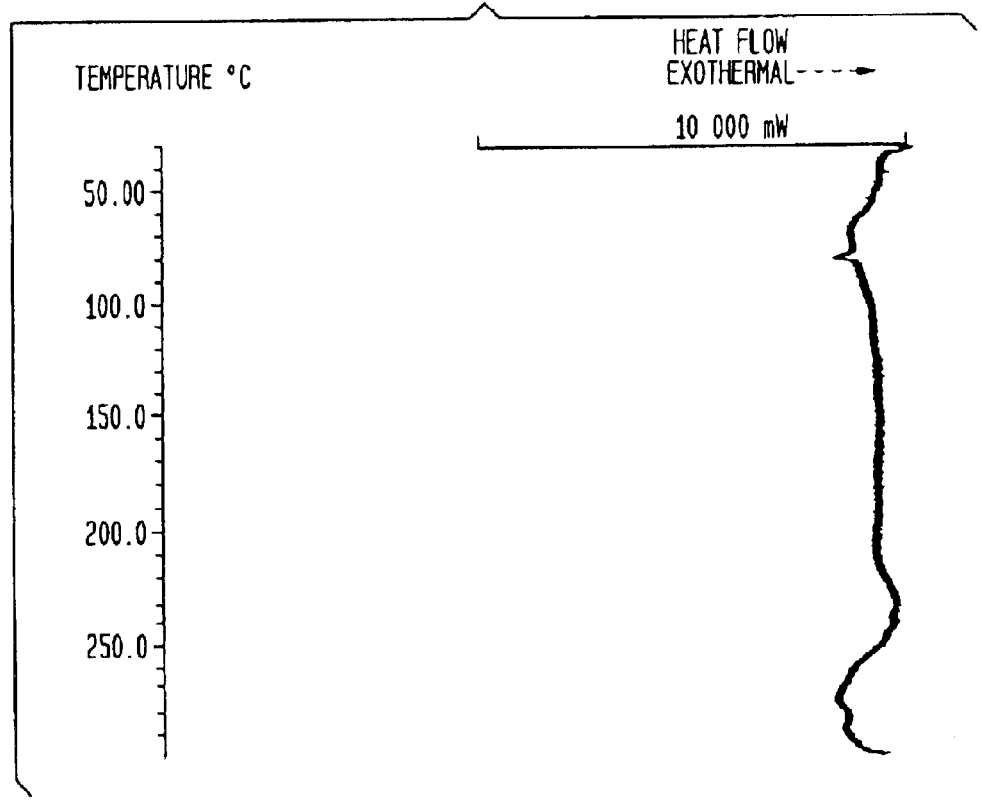
FIG. 1D is a DSC thermogram of an inclusion complex of fenofibrate with beta cyclodextrin.

Thermograms of fenofibrate, beta cyclodextrin, a physical mixture of fenofibrate and beta cyclodextrin in a molar ratio 1:1 and the fenofibrate-beta cyclodextrin inclusion complex of the invention were as shown in FIGS. 1A, 1B, 1C, and 1D respectively. The thermograms were taken with Mettler TC11K-DSC, manufactured by Mettler Instruments AG, Switzerland. The peak at 80.1° C. in FIG. 1A was due to the melting of fenofibrate. FIG. 2B showed an endothermic peak at 303.3° C. corresponding to beta cyclodextrin and one peak at 96° C. due to the moisture content of beta cyclodextrin. The physical mixture showed endothermic peaks of both fenofibrate at 79.8° C. and beta cyclodextrin at 299.9° C. as in FIG. 1C. The inclusion complex showed an drastic reduction in the intensity of the fenofibrate peak at 79.4° C. as in FIG. 1D, indicating the formation of inclusion complex.

EXAMPLE 15

In this example, in-vitro dissolution of the fenofibrate inclusion complexes of the invention and fenofibrate (micronized form) were performed using the rotating blade method at 75 rpm according to the USP24, in a dissolution medium constituted by water with 0.025 M sodium lauryl sulphate and water with 2% by weight polysorbate-80. The results were as shown in Table 5 below.

TABLE 5

| Sample No | Dissolution Medium | Volume of dissolution medium | Time (Mins) | #1 Run | #2 Run | #3 Run | #4 Run |
|---|---|---|---|---|---|---|---|
| 1 | Water with 0.025 M sodium lauryl sulfate. | 1200 ml | 5 | 73–76 | 8–10 | 55–81 | 11–29 |
| | | | 10 | 90–93 | 16–22 | 98–101 | 50–67 |
| | | | 20 | 100–102 | 24–30 | 99–102 | 79–85 |
| 2 | Water with 2% by weight polysorbate -80 | 1200 ml | 5 | 38–44 | 4–8 | 30–52 | 10–13 |
| | | | 10 | 60–65 | 19–22 | 72–79 | 30–37 |
| | | | 20 | 78–84 | 30–32 | 88–92 | 76–79 |
| | | | 30 | 92–95 | 36–38 | 98–101 | 84–88 |

1 run shows the % release of fenofibrate from the fenofibrate inclusion complex of Example 1 of the invention containing 160 mg of fenofibrate.
2 run illustrates the % release of fenofibrate from 160 mg fenofibrate raw material.
3 run shows the % release of fenofibrate from the fenofibrate tablets of Example 14 of the invention containing 160 mg of fenofibrate.
4 run shows the % release of fenofibrate from the commercial marketed product Supralip ® 160 mg tablets, manufactured by Fournier Pharmaceuticals LTD.

The results of #1 and #3 runs demonstrate that the fenofibrate inclusion complexes prepared by the method of invention showed a high in-vitro fenofibrate release as compared to the micronized fenofibrate raw material and marketed commercially available product, indicated by the results of #2 and #4 runs.

Thus, while there have been described what are presently believed to be the preferred embodiments of the present invention, those skilled in the art will appreciate that other and further modifications can be made without departing from the true scope of the invention, and it is intended to include all such modifications and changes as come within the scope of the claims as appended herein.

What is claimed is:

1. An inclusion complex which comprises fenofibrate of the formula 1:

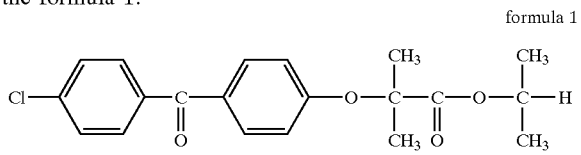

formula 1 with cyclodextrin, wherein said fenofibrate is in a micronized form having an average particle size of from about 1 μm to about 40 μm, said cyclodextrin having an average particle size of from about 10 μm to about 250 μm, wherein the molar ratio of fenofibrate to cyclodextrin is from about 1:0.5 to about 1:4.

2. The inclusion complex according to claim 1, wherein said fenofibrate has a micronized average particle size of from about 2 μm to about 20 μm.

3. The inclusion complex according to claim 1, wherein the cyclodextrin of the inclusion complex is beta cyclodextrin, gamma cyclodextrin, hydroxypropyl beta cyclodextrin, randomly methylated beta cyclodextrin or mixtures thereof.

4. The inclusion complex according to claim 1, wherein the molar ratio of fenofibrate to cyclodextrin is from about 1:0.5 to about 1:3.

5. A method for the preparation of an inclusion complex including fenofibrate of the formula 1:

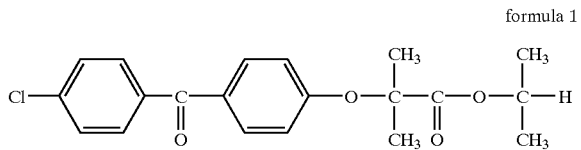

formula 1 with cyclodextrin, which method comprises:
a) wetting cyclodextrin having an average particle size of from about 10 μm to about 250 μm with a solvent selected from the group consisting of water, acetone, C1–C4 aliphatic alcohol other than ethanol or rectified spirit, and mixtures thereof, said solvent in an amount sufficient to form a semisolid mixture;
b) mixing the resulting semisolid mixture with micronized fenofibrate having an average particle size of from about 1 μm to about 40 μm thereby forming a mixed fenofibrate-cyclodextrin inclusion complex; and
c) drying said mixed inclusion complex at from about 40° C. to about 80° C. to form said fenofibrate-cyclodextrin inclusion complex, wherein the molar ratio of fenofibrate to cyclodextrin is from about 1:0.5 to about 1:4, wherein further the molar ratio of solvent to cyclodextrin is from about 1:1.5 to about 1:4.

6. The method according to claim 5, wherein the fenofibrate is in micronized form having an average particle size of from about 2 μm to about 20 μm.

7. A method according to claim 5, wherein the solvent is water, isopropyl alcohol or mixtures thereof, wherein the molar ratio of water to alcohol is from about 1:9 to about 9:1.

8. A method according to claim 5, wherein the cyclodextrin of the Inclusion complex is beta cyclodextrin, gamma cyclodextrin, hydroxypropyl beta cyclodextrin, randomly methylated beta cyclodextrin or mixtures thereof.

9. A method according to claim 5, wherein the molar ratio of fenofibrate to cyclodextrin is from about 1:0.5 to about 1:3.

10. A pharmaceutical formulation of fenofibrate of the formula 1:

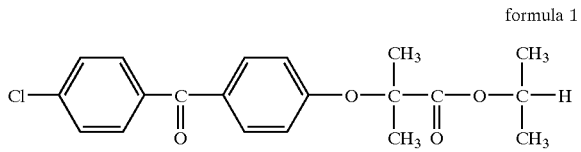

formula 1 with cyclodextrin and a pharmaceutically acceptable excipient, wherein said fenofibrate is in micronized from having an average particle size of from about 1 μm to about 40 μm, said cyclodextrin having an average particle size of about 10 μm to about 250 μm, wherein further the molar ratio of fenofibrate to cyclodextrin is from about 1:0.5 to about 1:4.

11. The pharmaceutical formulation according to claim 10, wherein said fenofibrate is in micronized form having an average particle size of from about 2 μm to about 20 μm.

12. The pharmaceutical formulation according to claim 10, wherein the cyclodextrin of the inclusion complex is beta cyclodextrin, gamma cyclodextrin, hydroxypropyl beta cyclodextrin, randomly methylated beta cyclodextrin or mixtures thereof.

13. The pharmaceutical formulation according to claim 10, wherein said excipient includes lactose, microcrystalline cellulose, calcium carbonate, starch, colloidal silicone dioxide, sodium starch glycolate, talc, magnesium stearate, polyvinyl pyrrolidone, mixtures thereof.

14. The pharmaceutical formulation according to claim 10, wherein the molar ratio of fenofibrate to cyclodextrin is from about 1:0.5 to about 1:3.

15. A tablet comprising a pharmaceutical formulation prepared according to claim 10.

16. A capsule comprising a pharmaceutical formulation prepared according to claim 10.

17. A method for the preparation of a pharmaceutical formulation of an inclusion complex of fenofibrate of the formula 1:

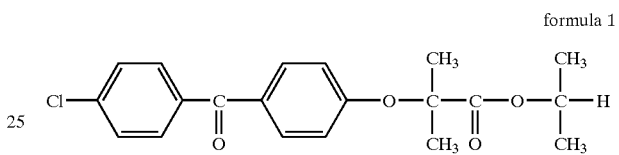

formula 1 with cyclodextrin said method comprising mixing said inclusion complex of fenofibrate and cyclodextrin with an effective amount of a pharmaceutically acceptable excipient, wherein said fenofibrate is in micronized form having an average particle size of from about 1 μm to about 40 μm, said cyclodextrin having an average particle size of from about 10 μm to about 250 μm, wherein further the molar ratio of fenofibrate to cyclodextrin is from about 1:0.5 to about 1:4.

18. The method according to claim 17, wherein said fenofibrate is in a micronized form having an average particle size of from about 2 μm to about 20 μm.

19. The method according to claim 17 wherein said cyclodextrin of the inclusion complex is beta cyclodextrin, gamma cyclodextrin, hydroxypropyl beta cyclodextrin, randomly methylated beta cyclodextrin or mixtures thereof.

20. The method according to claim 17, wherein the molar ratio of fenofibrate to cyclodextrin is from about 1:1 to about 1:2.

* * * * *